United States Patent
Spenser et al.

(10) Patent No.: US 8,545,533 B2
(45) Date of Patent: Oct. 1, 2013

(54) GUIDEWIRE STOP

(75) Inventors: Benjamin Spenser, Hof Karmel (IL);
Uri Rosenschein, M.P. Merkaz (IL); Gil Ofir, Even Yehuda (IL)

(73) Assignee: Gardia Medical Ltd., Caesarea (IL)

( * ) Notice: Subject to any disclaimer, the term of this patent is extended or adjusted under 35 U.S.C. 154(b) by 152 days.

(21) Appl. No.: 12/768,003

(22) Filed: Apr. 27, 2010

(65) Prior Publication Data

US 2010/0204725 A1 Aug. 12, 2010

Related U.S. Application Data

(62) Division of application No. 11/873,893, filed on Oct. 17, 2007, now abandoned.

(51) Int. Cl.
*A61M 29/00* (2006.01)

(52) U.S. Cl.
USPC .......................................................... 606/200

(58) Field of Classification Search
USPC ............... 606/200; 600/434, 585; 623/1.11, 623/1.12, 1.15, 1.16, 1.22
See application file for complete search history.

(56) References Cited

U.S. PATENT DOCUMENTS

| | | | |
|---|---|---|---|
| 4,425,908 A | 1/1984 | Simon | |
| 5,848,964 A | 12/1998 | Samuels | |
| 5,972,019 A | 10/1999 | Engelson et al. | |
| 6,099,549 A | 8/2000 | Bosma et al. | |
| 6,179,859 B1 | 1/2001 | Bates et al. | |
| 6,254,525 B1 | 7/2001 | Reinhardt et al. | |
| 6,371,971 B1 | 4/2002 | Tsugita et al. | |
| 6,432,122 B1 | 8/2002 | Gilson et al. | |
| 6,537,295 B2 | 3/2003 | Petersen | |
| 6,544,231 B1 * | 4/2003 | Palmer et al. | 604/165.01 |
| 6,656,195 B2 * | 12/2003 | Peters et al. | 606/159 |
| 6,656,202 B2 | 12/2003 | Papp et al. | |
| 6,878,291 B2 | 4/2005 | Lowe et al. | |

(Continued)

FOREIGN PATENT DOCUMENTS

| | | |
|---|---|---|
| DE | 19846630 | 4/2000 |
| WO | WO 02/40090 | 5/2002 |

OTHER PUBLICATIONS

Topol et al., "Recognition of the Importance of Embolization in Athereosclerotic Vascular Disease," Circulation, 101:570-580, (2000).

(Continued)

*Primary Examiner* — Gary Jackson
*Assistant Examiner* — Jonathan Hollm
(74) *Attorney, Agent, or Firm* — Novak Druce Connolly Bove + Quigg LLP (57) ABSTRACT

A user-actuatable guidewire stop is disclosed which can be used to stop and/or lock a medical device on a guidewire advanced through a body lumen. The guidewire stop is configured as a coil spring having an inner lumen configured to slideably and rotationally receive the guidewire in an unlocked configuration, and to frictionally engage the guidewire in a locked configuration. The coil spring is composed of turns having at least one protrusion disposed on a turn of the coil spring and adapted for engagement with a corresponding recess disposed on an adjacent turn of the coil spring, wherein the at least one protrusion interlocks with the corresponding recess to maintain the coil spring in the unlocked configuration. The coil spring transitions into the unlocked configuration by disengaging the at least one protrusion from the corresponding recess.

9 Claims, 8 Drawing Sheets

(56) References Cited

U.S. PATENT DOCUMENTS

| | | | |
|---|---|---|---|
| 7,678,129 B1* | 3/2010 | Gesswein et al. | 606/200 |
| 2002/0062133 A1 | 5/2002 | Gilson et al. | |
| 2002/0082558 A1 | 6/2002 | Samson et al. | |
| 2002/0091407 A1 | 7/2002 | Zadno-Azizi et al. | |
| 2002/0091408 A1 | 7/2002 | Sutton et al. | |
| 2002/0095174 A1 | 7/2002 | Tsugita et al. | |
| 2002/0111671 A1* | 8/2002 | Stenzel | 623/1.16 |
| 2002/0138094 A1 | 9/2002 | Borillo et al. | |
| 2002/0151927 A1 | 10/2002 | Douk et al. | |
| 2002/0165574 A1 | 11/2002 | Ressemann et al. | |
| 2002/0165598 A1 | 11/2002 | Wahr et al. | |
| 2002/0183782 A1 | 12/2002 | Tsugita et al. | |
| 2003/0225435 A1 | 12/2003 | Huter et al. | |
| 2004/0098032 A1 | 5/2004 | Papp et al. | |
| 2004/0102789 A1* | 5/2004 | Baughman | 606/99 |
| 2004/0116996 A1* | 6/2004 | Freitag | 623/1.11 |
| 2004/0167566 A1 | 8/2004 | Neulke et al. | |
| 2004/0199198 A1 | 10/2004 | Beulke et al. | |
| 2005/0021075 A1 | 1/2005 | Bonnette et al. | |
| 2006/0015139 A1 | 1/2006 | Tsugita et al. | |
| 2007/0162071 A1 | 7/2007 | Burkett et al. | |

OTHER PUBLICATIONS

International Search Report for PCT Application No. PCT/IB2008/051156, dated Feb. 17, 2009.

* cited by examiner

GUIDEWIRE STOP

CROSS-REFERENCE TO RELATED APPLICATIONS

This application claims the benefit of priority to and is a divisional application of U.S. patent application Ser. No. 11/873,893 filed Oct. 17, 2007, the disclosure of which is incorporated herein by reference in its entirety.

FIELD OF THE INVENTION

The present invention relates generally to the field of medical procedures which employ a guidewire. In particular, the present invention relates to an actuatable guidewire stop capable of stopping and/or locking a medical device on a guidewire at a location in the body lumen defined by the user.

BACKGROUND OF THE INVENTION

Transcatheter procedures are employed in increasing numbers for opening stenosed or occluded blood vessels in patients caused by deposits of plaque or other materials on the walls of the blood vessels. Such minimally invasive procedures have proven to be advantageous compared to traditional surgical procedures, such as open heart surgery. Stenosis in arteries and other blood vessels can be treated by permanently or temporarily introducing a stent into the stenosed region to open the lumen of the vessel.

However, embolic material may be released into the blood stream during implantation of a stent or another prosthetic device, placing the patient at great risk. Embolic material formed of calcium deposits, intimal debris, pieces of artheromatous plaque and/or thrombi has the potential of migrating downstream and causing distal tissue damage, for example stroke or myocardial infarction (see Topol, E. J. and Yadov, J. S., "Recognition of the Importance of Embolization in Athereosclerotic Vascular Disease", Circulation 2000, 101: 570). Embolic material which can potentially damage the distal tissue is often released during vascular intervention procedures, such as stenting of an artheromatous region. To alleviate this problem, an embolic filter may be advanced to a site distal to the treatment site to filter and capture undesired embolic material from the blood. The filter is typically formed from a mesh material mounted on an expansion frame adapted to open from a contracted (or collapsed) state to a deployed (or open) state. The filter is typically inserted over or together with a guidewire using a delivery catheter. Following the treatment procedure, the filter is collapsed and removed from the body over the guidewire or together with the guidewire. Additional treatment devices, such as balloons and stents, can be inserted and removed via the same guidewire.

The filter should be positioned at a location as close as possible distal of the treatment site to ensure that most or all of the embolic debris is trapped by the filter. On the other hand, the guidewire should extend as far as possible into the body lumen to stabilize the treatment site. It is extremely difficult to achieve both these objectives simultaneously when using a built-in filter stop, because accurate placement of the stop relative to the treatment site by fluoroscopic observation is very difficult.

Therefore, there is a need for a guidewire stop capable of being stopped/locked on a bare guidewire, i.e. a guidewire section devoid of a preformed or fixedly attached stop. There is also a need for an intravascular treatment device capable of being stopped and/or locked on the guidewire at any user-selectable position following deployment of the treatment device in the body lumen.

SUMMARY OF THE INVENTION

The present invention relates to a user-actuatable guidewire stop which can be used to stop and/or lock a medical device on a guidewire advanced through a body lumen. It will be appreciated that this provides the user with a significant advantage, since instead of the medical device being preassembled onto the guidewire as is known in the art, the present invention allows for the user to determine precisely where the medical device is to be placed after the guidewire has been introduced into the body. This is of particular significance, especially when dealing with occluded blood vessels where it is crucial to place an embolic filter at a location where virtually all embolic debris will be trapped. The term "guidewire" as employed in the present disclosure is intended to refer to any elongated member used to facilitate the advancement of other elements through body lumens. The guidewire may be any standard, non-dedicated guidewire known in the art. There is no need for dedicated guidewire. After the guidewire stop is locked onto the guidewire, the proximal length of the guidewire is available for use for any other purpose or with additional medical devices. While some embodiments of the invention will be described with reference to an embolic filter, it will be appreciated that the guidewire stop of the invention may be useful for any medical device that is designed to be introduced into a body lumen through the use of a guidewire. Thus, the medical device may be adapted for temporary or permanent implantation into any of the body's systems, such as, but not limited to, urological, neurological, or cardiological. It is also appreciated that the state of the art is such that new medical devices are continuously being developed which are designed for implantation into a body lumen via a transcatheter procedure. The guidewire lock of the present invention provides a unique solution for the positioning of such devices with respect to a guidewire. According to one aspect of the invention, an actuatable guidewire stop configured to limit movement of an intravascular device relative to a guidewire includes a coil spring having an inner lumen with a first diameter configured to slideably and rotationally receive the guidewire in an unlocked configuration, and to frictionally engage the guidewire in a locked configuration, wherein in the locked configuration the inner lumen has a second diameter smaller than the first diameter.

According to another aspect of the invention, an actuatable guidewire stop configured to limit movement of an intravascular device relative to a guidewire includes a tubular member having one or more resilient members formed in a peripheral opening thereof and exerting a radially inward bias force, the tubular member surrounding the guidewire, and a restraining member interposed between the tubular member and the guidewire to maintain the guidewire stop in an unlocked configuration on the guidewire. Upon removal of the restraining member from a space between the tubular member and the guidewire, the resilient member frictionally engages the guidewire and locks the guidewire stop to the guidewire.

According to yet another aspect of the invention, an intravascular filter device includes a filter frame disposed about a guidewire, a filter membrane operatively coupled to the filter frame, and a coil spring attached to the filter frame. The coil spring has an inner lumen with a first diameter configured to slideably and rotationally receive the guidewire in an unlocked configuration, and frictionally engage the guidewire in a locked configuration, wherein in the locked configuration the inner lumen has a second diameter smaller than the first diameter. In this embodiment, a medical device is connected to the guidewire stop such that locking of the stop onto the guidewire causes the medical device to become locked to the guidewire as well. In other embodiments, the guidewire stop may be independent from the medical device.

The invention is further directed to a method for locking a guidewire stop onto a guidewire at a desired location along the length of the guidewire, with the steps of advancing a guidewire stop configured as a coil spring having an inner lumen with a first diameter configured to slideably and rotationally receive the guidewire in an unlocked configuration to the desired location, and removing a restraining member which maintains the coil spring in the unlocked configuration, thereby causing the coil spring to frictionally engage the guidewire in a locked configuration and lock the guidewire stop on the guidewire, wherein in the locked configuration the inner lumen has a second diameter smaller than the first diameter.

Embodiments of the invention may include one or more of the following features.

In certain embodiments, the inner lumen of the coil spring may have the first diameter when a longitudinal or radially outward force is applied to the coil spring, and the inner lumen may have a second diameter without an external force being applied to the coil spring.

In certain embodiments, the guidewire stop may include a restraining member configured to urge the coil spring into the unlocked configuration, wherein the coil spring assumes the locked configuration upon removal of the restraining member. The restraining member may be a tubular member disposed between an inner surface of the coil spring and the guidewire, with an inner diameter of the tubular restraining member being greater than an outside diameter of the section of the guidewire. In other embodiments, the restraining member may be disposed between adjacent turns of the coil spring, wherein the restraining member urges the adjacent turns apart so that the coil spring assumes the unlocked configuration, and wherein the coil spring assumes the locked configuration upon removal of the restraining member. The restraining member may be implemented as a wire or filament.

In still other embodiments, the restraining member may be disposed along turns of the coil spring and may include at least one protrusion on a turn adapted for engagement with a corresponding recess of an adjacent turn, wherein the protrusion interlocks with the corresponding recess to maintain the coil spring in the unlocked configuration. The recess may have a predetermined undercut angle.

In other embodiments, the restraining member may include a wire or filament disposed external to and in an axial direction of the coil spring, wherein the wire or filament is affixed to turns of the coil spring by a connection having a rated break point so as to maintain the coil spring in the unlocked configuration, and wherein removal of the wire or filament causes the coil spring to assume the locked configuration on the guidewire. The wire or filament may have a doubled-over configuration with respect to the coil spring and may be affixed to the coil spring by welding spots.

In certain embodiments, the guidewire stop may include an actuator operatively coupled to a proximal portion of the coil spring for changing the coil spring from the unlocked configuration to the locked configuration. In other embodiments, the actuator may be operatively coupled to a proximal portion of the tubular member for proximally removing the tubular member to change the coil spring from the unlocked configuration to the locked configuration.

The locking element, for example, the coil spring or tubular member, may be formed from an elastic material or a shape-memory material such as Nitinol.

The guidewire stop may further include an actuator implemented as a pulling wire, wherein the actuator can be withdrawn together with the restraining member from the body and such that the proximal length of the guidewire is unobstructed and can be used for other purposes.

These and other features and advantages of the present invention will become more readily appreciated from the detailed description of the invention that follows.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

FIG. 5b shows planar views of the surface of the tubular locking element of FIG. 5a;

DETAILED DESCRIPTION OF CERTAIN ILLUSTRATED EMBODIMENTS

The disclosed devices are directed to guidewire stops (or locks) capable of locking on a bare guidewire, i.e., a guidewire that does not include stops or locks applied to or formed on the guidewire prior to insertion of the guidewire into the body lumen. The approach allows the clinician to use in conjunction with a specific medical device any guidewire suitable for a procedure regardless of the design of the guidewire or its intended use.

The disclosed guidewire stops have a flexible or resilient body with an inner lumen configured to slideably and rotationally receive a guidewire in an unlocked position and to frictionally engage the guidewire in a locked position. A user-activated actuator enables the user to place the guidewire stop, with or without an attached medical device, such as an embolic protection filter, at any desired location along the guidewire. Placement of the guidewire stop can be monitored in a conventional manner, for example, by fluoroscopic observation using radiopaque markers.

Figure 1A:
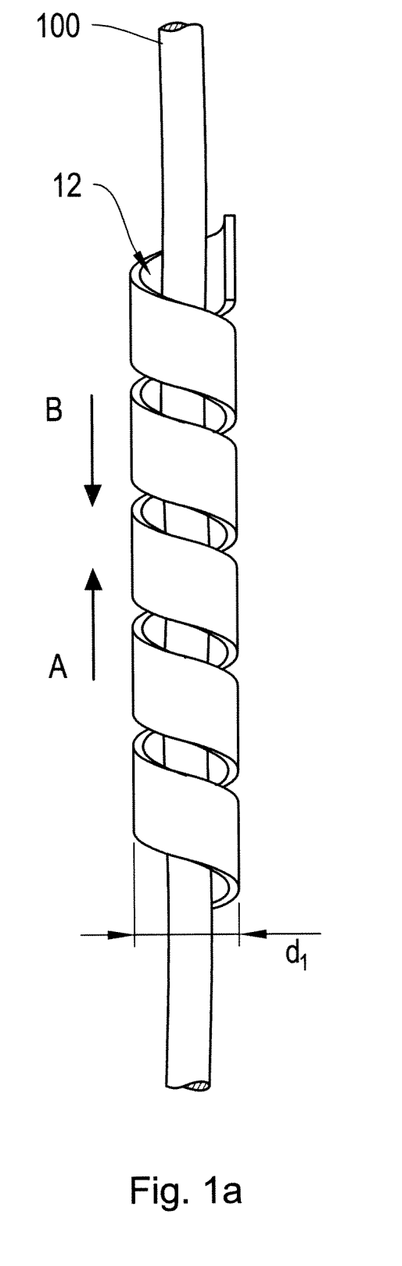
FIGS. 1a and 1b show schematically in a perspective view an exemplary embodiment of a guidewire stop according to the invention, wherein the guidewire stop locking element comprises a single coil spring.
Figure 1B:
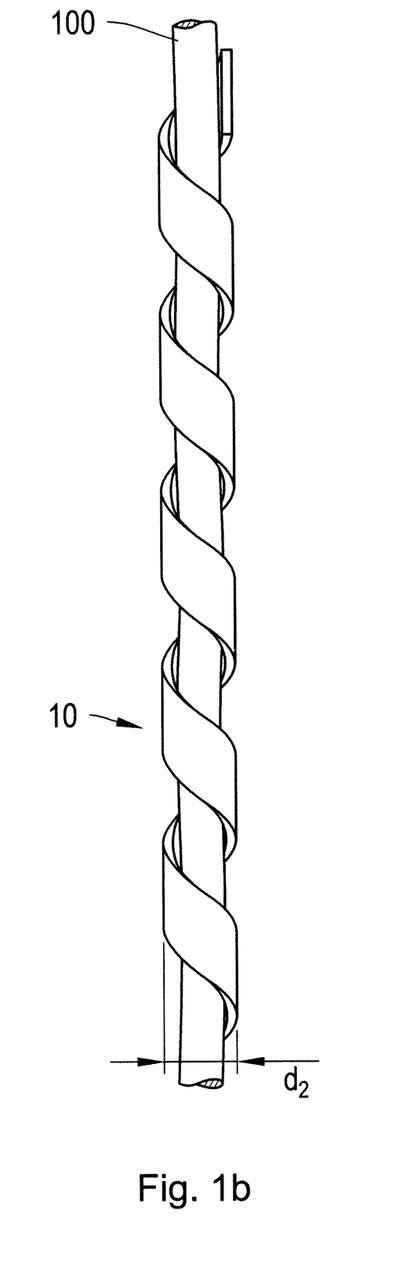

In one exemplary embodiment of the invention shown schematically in FIGS. 1a and 1b, a coil spring 10 defines an inner lumen 12 through which a guidewire 100 passes. The spring 10 is intrinsically biased to contract and lock along the guidewire 100 with an outside diameter $d_1$ (locked configuration, FIG. 2b), preventing further movement of the coil spring 10 with respect to the guidewire 100. When a force indicated by arrows A and B is applied in the longitudinal direction between the two ends of the coil spring 10, the spring is compressed and can move freely with respect to guidewire 100 (unlocked configuration, FIG. 2a). In the unlocked configuration, coil spring 10 has a larger diameter $d_2$. An actuating element adapted to be used for applying the longitudinal force along A and B is not shown so as not to obscure the drawing.

In operation, the coil spring 10 is moved in the unlocked configuration over the guidewire 100 to an area in the body lumen where a medical procedure is to be performed. The actuating element (not shown) is moved away from the spring ends, causing the spring to lock on the guidewire 100 at a user-defined location.

Figure 2A:
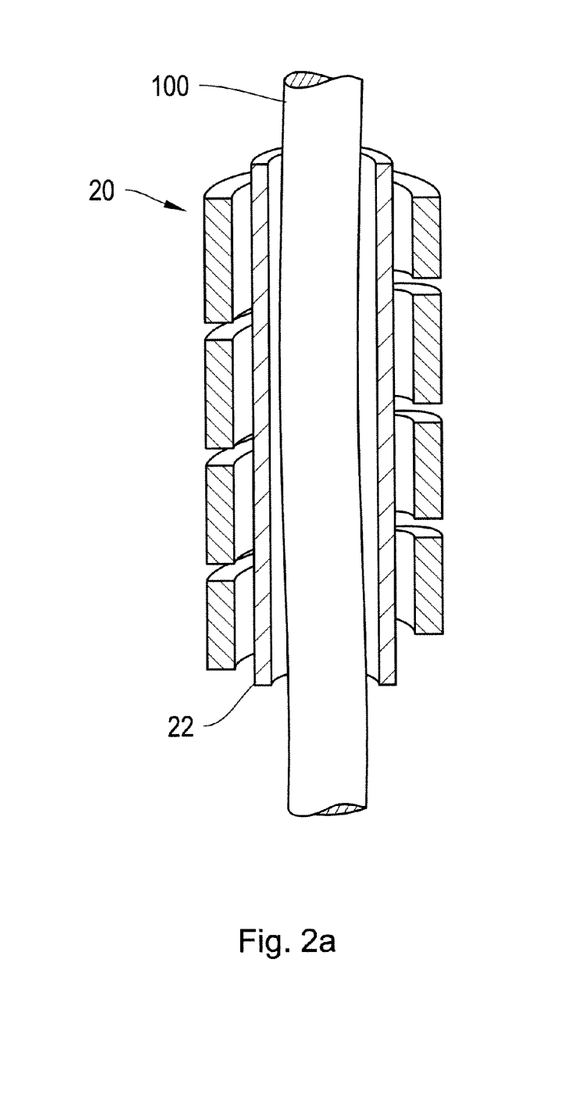
FIGS. 2a and 2b show schematically in cross section other exemplary embodiments of a guidewire stop according to the invention using a coil spring.

The embodiment illustrated in FIG. 2a is similar to that of FIGS. 1a and 1b, with the exception that the coil spring 20 is maintained in an unlocked configuration by a restraining sheath 22 disposed between the guidewire 100 and the coil spring 20. When the restraining sheath 22 is withdrawn from the space between guidewire 100 and coil spring 20, coil spring 20 automatically constricts and locks around guidewire 100, as before. It is appreciated that in this embodiment as well as in others disclosed herein, any suitable activating means may be employed for removing the restraining sheath 22, so as to activate the spring 20. In this embodiment, for example, a pulling wire or activation catheter may be coupled to the restraining sheath 22 (or formed as a unit with the restraining sheath 22) for enabling the user to withdraw the restraining sheath 22 from the space between the guidewire 100 and the coil spring 20.

Figure 2B:
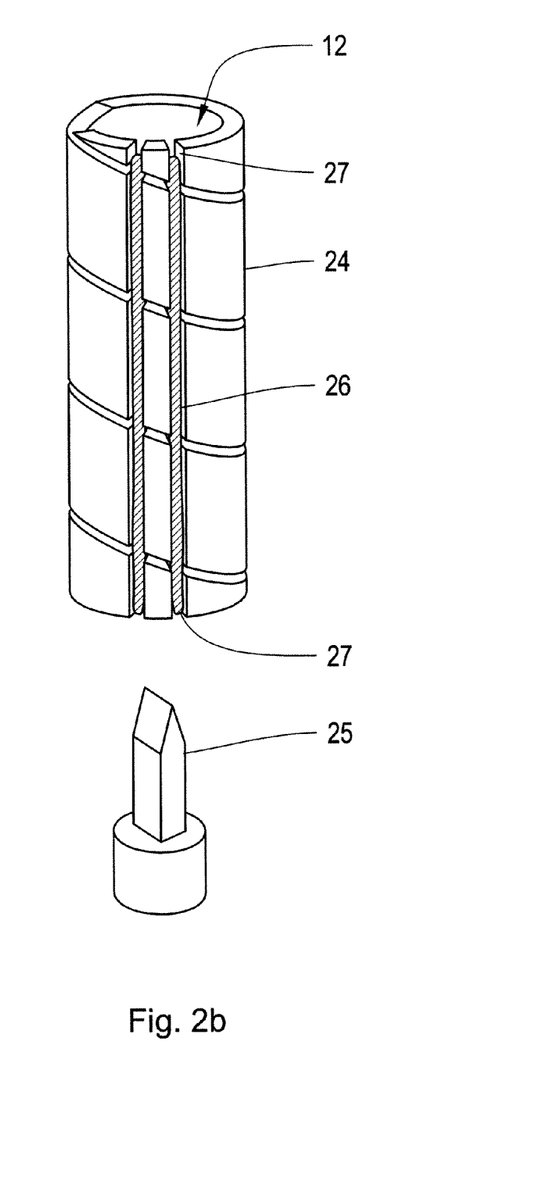

In another embodiment of a coil spring shown in FIG. 2b, the coil spring 24 is held in an open, unlocked configuration by at least one restraining filament 26 which runs longitudinally along substantially the length of the spring 24. Any suitable number of filaments, i.e. one or more filaments, may be provided to restrain the spring 24 in the open configuration; two filaments are illustrated for the sake of example only. The filament(s) 26 may be looped through notches 27 disposed at the ends of spring 24. In addition, the filaments may be routed in longitudinal recesses disposed on the outside or inside, or both, of the spring 24, so as to maintain the outside and/or inside diameter of the spring 24 within acceptable limits. When the filament(s) 26 is/are cut, the coil spring 24 automatically contracts around a guidewire positioned therein (not shown), so as to lock the spring 24 to the guidewire. In one embodiment, the filament may be severed by actuating means, such as an activation catheter having a sharp end 25 adapted for cutting the filament(s).

Figure 3A:
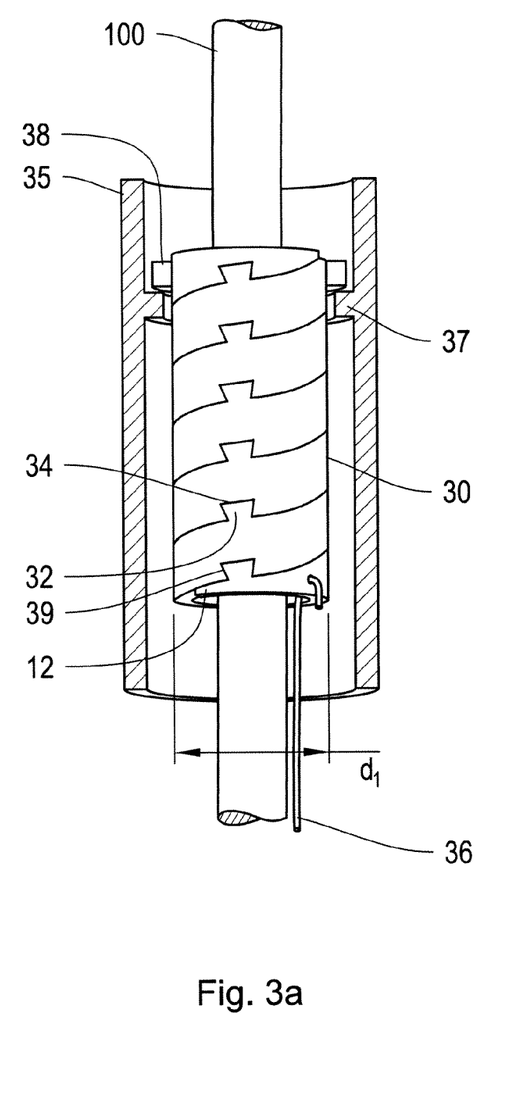
FIGS. 3a and 3b show schematically another exemplary embodiment of a guidewire stop according to the invention.
Figure 3B:
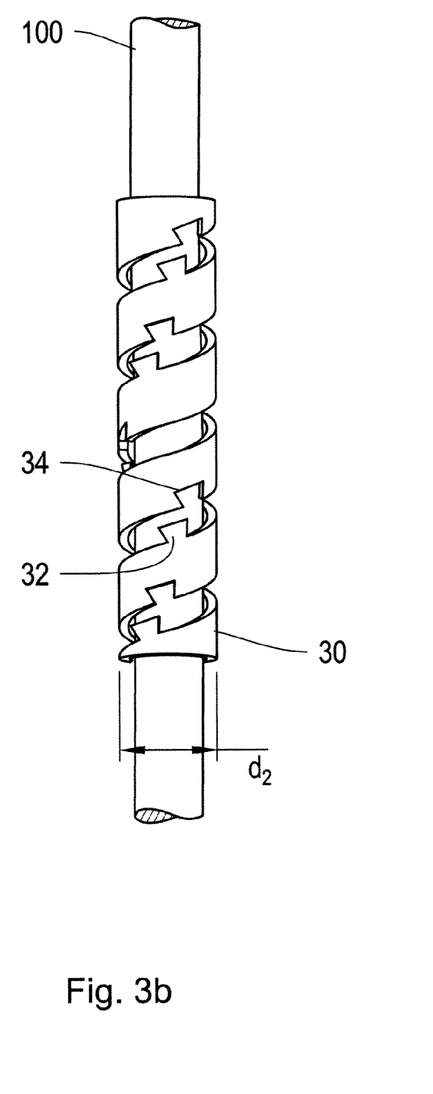
Figure 3C:
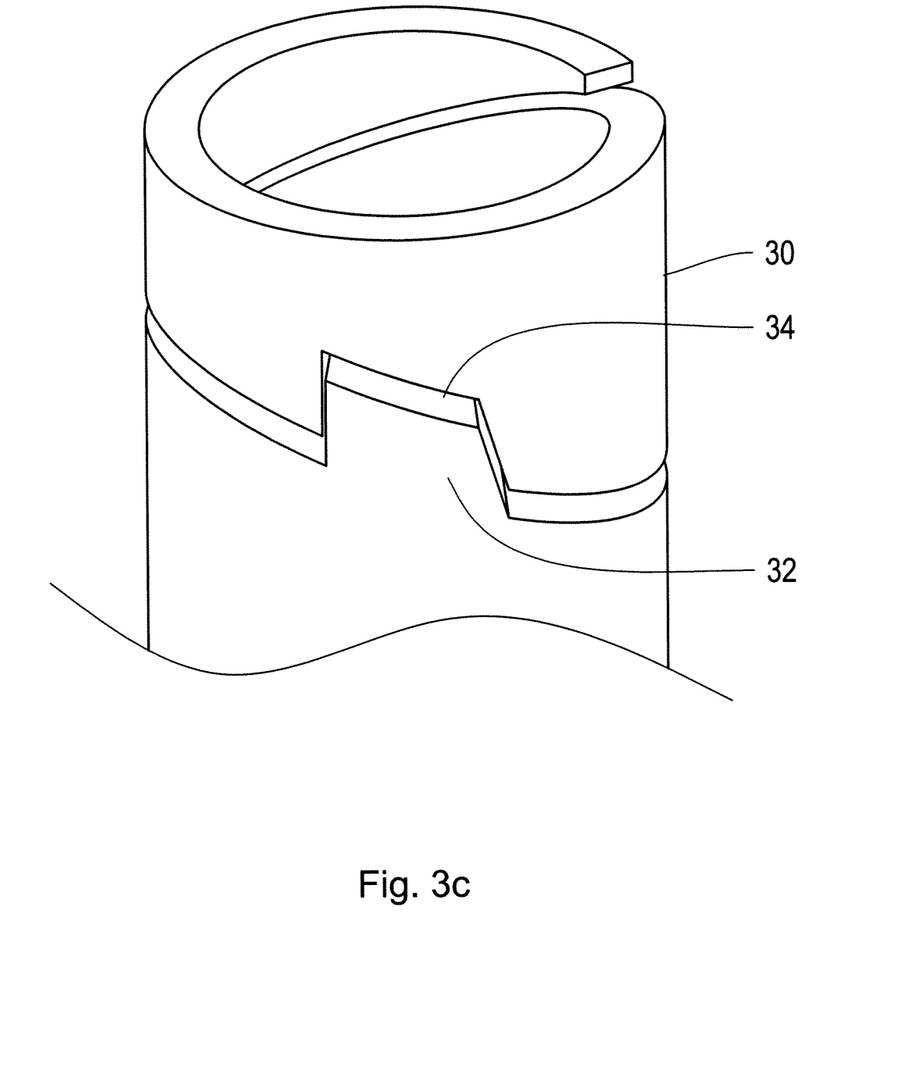
FIG. 3c shows a detail of the guidewire stop of FIGS. 3a and 3b.

FIGS. 3a-3c illustrate another embodiment of the present invention in which the restraining means, meaning the structure that prevents the biased spring to collapse onto and lock on the guidewire, are formed as an integral part of a coil spring 30. In this embodiment, protrusions 32 are formed on the turns of the coil spring 30, with the protrusions 32 adapted to engage in corresponding indentations 34 located on an adjacent turn of the spring 30 in an unlocked configuration. FIG. 3a shows spring 30 in an unlocked configuration with the aforementioned diameter $d_1$ (see FIG. 1a), allowing spring 30 to slide along guidewire 100. The configuration in the compressed, unlocked configuration of coil spring 30 is more clearly shown in FIG. 3c, with each protrusion 32 engaging in a corresponding indentation 34, thereby maintaining coil spring 30 in the compressed, unlocked configuration. As shown in FIG. 3a, spring 30 may be retained in a retainer tube 35 (with may be part of a delivery catheter) which encircles coil spring 30 and may include an inward pointing shoulder 37 supporting coil spring 30 formed on an outer shoulder 38 of spring 30.

In the compressed, unlocked configuration (FIG. 3a), the protrusion/indentation pairs are interlocked through frictional force which prevents coil spring 30 from opening unintentionally to the stretched locked configuration shown in FIG. 3b with diameter $d_2$. The level of friction required to disengage the interlocked protrusion/indentation pairs is determined by an undercut angle 39 between a protrusion and the corresponding indentation. Application of a pulling force proximally along a pulling wire 36 causes each of the protrusions the coil spring 30 to disengage from the corresponding indentation, causing the coil spring 30 to open in the longitudinal direction and contract in the radial direction, as shown in FIG. 3b, thereby effectively locking the spring 30 to guidewire 100.

Figure 4A:
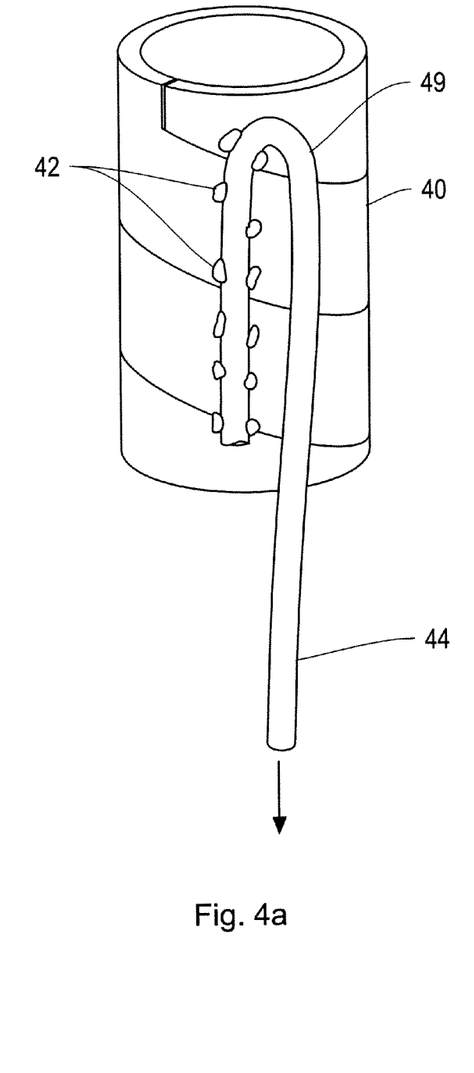
FIGS. 4a and 4b show schematically in a perspective view another exemplary embodiment of a guidewire stop according to the invention.
Figure 4B:
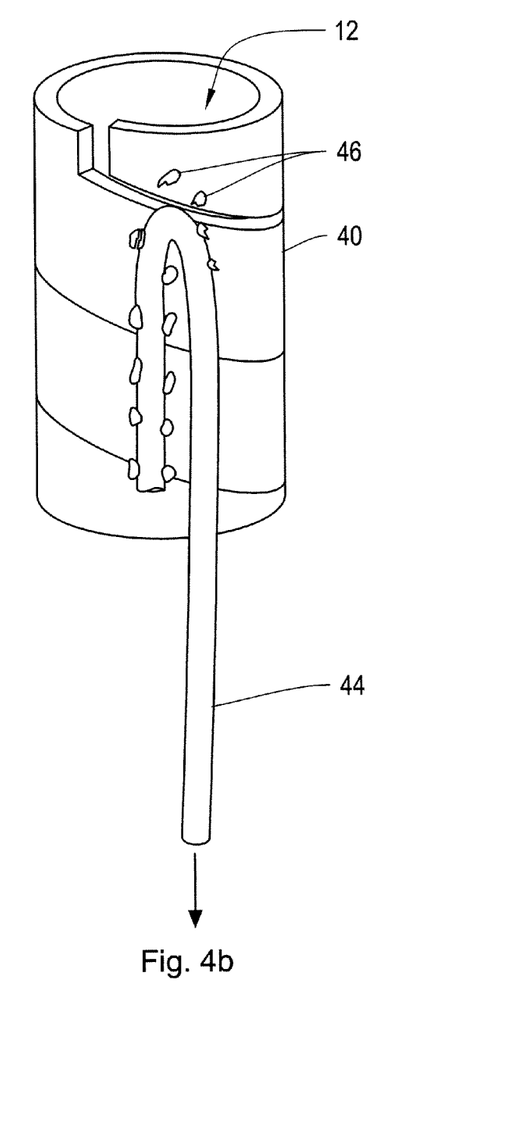

FIGS. 4a and 4b illustrate a coil spring 40 of the type shown FIGS. 1a and 2a. However, instead of being held in the unlocked configuration by an applied longitudinal force (FIG. 1a) or a retainer tube 22 (FIG. 2a), an actuating wire 44 is attached, for example, by spot welds 42, to the turns of coil spring 40 to maintain coil spring 40 in a larger-diameter, unlocked configuration. Actuating wire 44 is secured to the body of coil spring 40 in a doubled-over manner, with a bend 49 near the distal end of spring 40. As the user pulls proximally on actuating wire 44, spot welds 42 sequentially break off, starting with spot welds 46 near the bend 49, allowing the inwardly biased turns of coil spring 40 to gradually collapse and engage the guidewire (not shown). This causes coil spring 40 to revert to a relaxed, smaller-diameter state and lock on the guidewire due to the smaller diameter of the inner lumen 12 in coil spring 40. It will be appreciated that the illustrated arrangement of the welds 42 used to attach the actuating wire 44 and the disclosed bend 49 is meant to be only exemplary and that other arrangements and methods for attaching the actuating wire 44 to the helical coil 40 may be employed, such as soldering, crimping, gluing and the like.

Figure 5A:
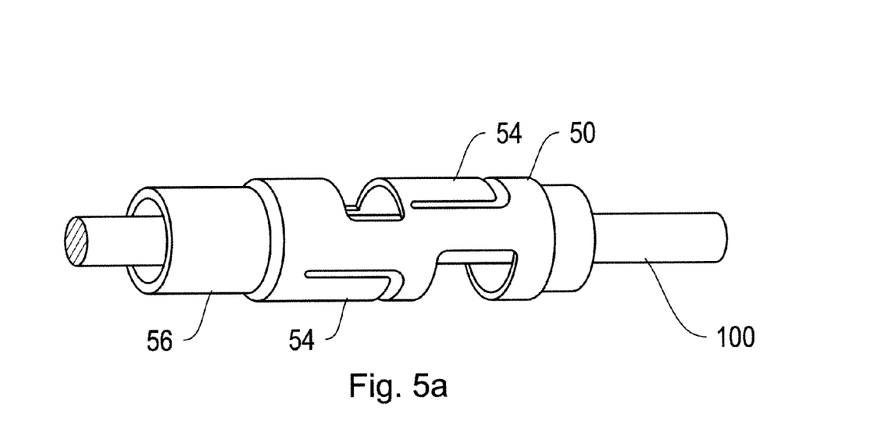
FIG. 5a shows schematically in a perspective view another exemplary embodiment of a guidewire stop.
Figure 5B:
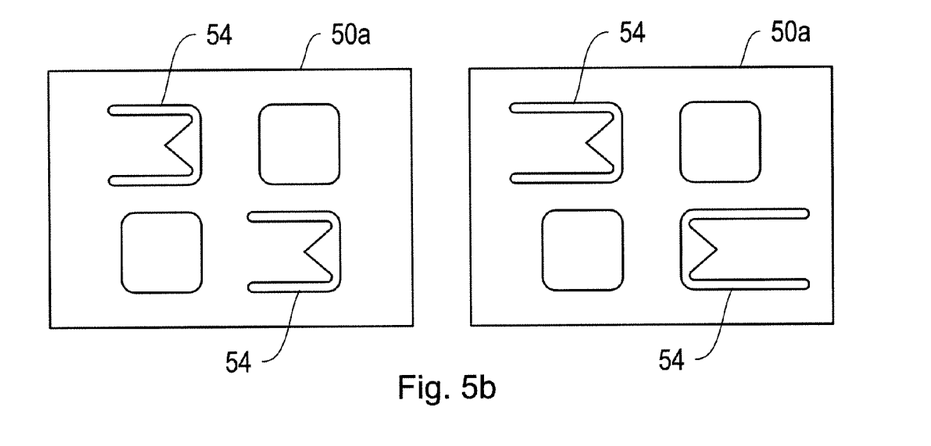
Figure 5C:
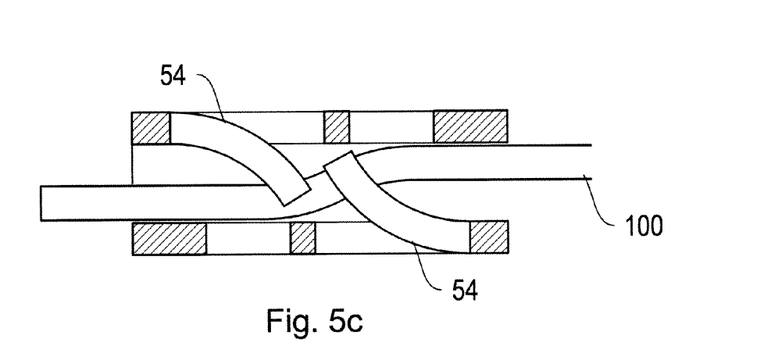
FIG. 5c shows engagement between the guidewire stop of FIG. 5a and the guidewire.

FIGS. 5a-5c illustrate another exemplary embodiment of a locking element 50 made of a tube having a plurality of windows 52 formed in the tube surface 50a (FIG. 5b), shown here as an unrolled representation of the tube surface. At least some of the windows 52 include inwardly biased protruding members 54 (or prongs) adapted to engage with guidewire 100 passing through the interior of locking element 50 after a restraining element 56 disposed between the locking element and guidewire 100 has been removed. The protruding members 54 may have the configuration shown in FIG. 5b or another suitable shape or orientation. For example, the protruding members 54 may be aligned lengthwise in the same direction (left side of FIG. 5b), or some of the members 54 may be aligned in the opposite direction of other members 54 (right side of FIG. 5b).

The locking element 50 operates as follows: in the unlocked configuration, tubular restraining element 56 interposed between locking element 50 and guidewire 100 prevents the protruding members 54 from contacting guidewire 100. Unillustrated actuating means (for example, a delivery catheter and a pulling wire similar to the embodiment depicted in FIG. 3a) may be employed to withdraw the restraining element 56 from the space between guidewire 100 and locking element 50. When restraining element 56 is withdrawn proximally, the protruding members 54 automatically extend inwardly so as to grip the guidewire 100 (see FIG. 5c)

and effectively lock the locking element 50 on the guidewire 100. It is noted that in FIG. 5c, the shaped protruding members (54) grip guidewire 100 from opposite directions. However, as noted above, many other configurations are possible for effectively gripping the guidewire, and the illustration is meant to be exemplary only.

It is appreciated that the guidewire used with the guidewire stop of the present invention may be any standard guidewire. A dedicated guidewire need not be employed. This provides a substantial advantage by providing the user with a greater degree of freedom as to where to position the medical device. The guidewire lock may be positioned on and locked to the guidewire with or without an attached medical device, such as an embolic protection filter.

Figure 6:
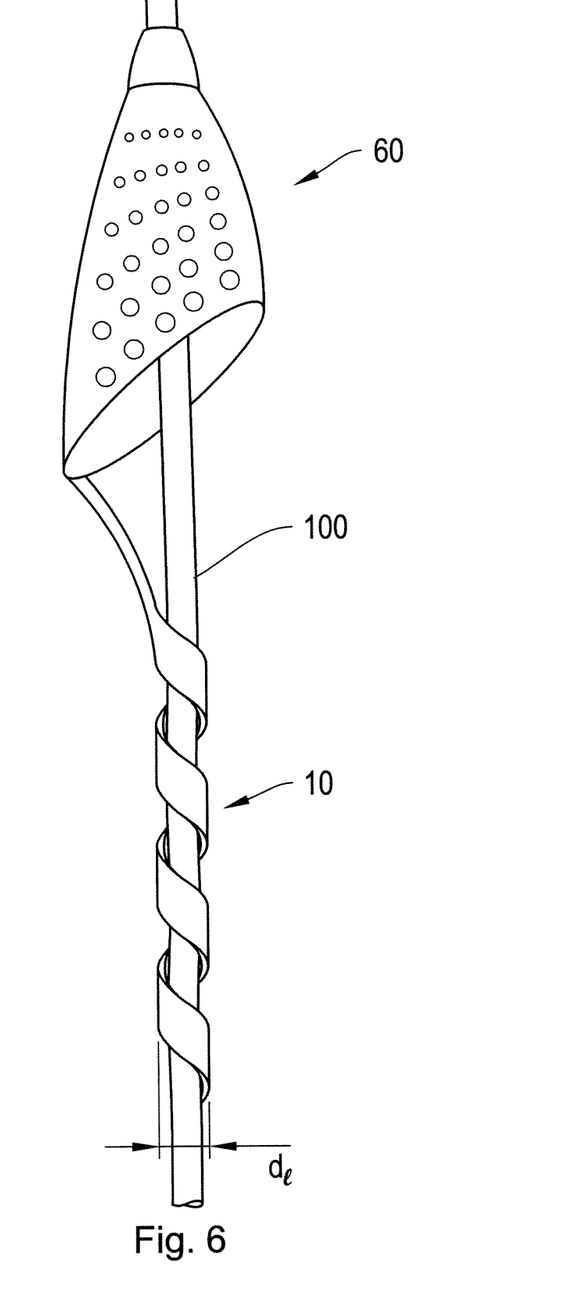
FIG. 6 shows schematically the guidewire stop of FIG. 1a with an attached embolic protection filter.

FIG. 6 shows schematically how an embolic protection filter 60 may be attached to a locking element, such as locking element 10 depicted in FIGS. 1a and 1b. Guidewire 100 is shown here as protruding from distal end of filter 60 in a manner known in the art. Filter 60 may include a filter frame which in the illustrated example is attached to a coil spring locking element 10 using a single strut 62; however, more than one strut can be employed. Filter 60 may be deployed conventionally using a delivery catheter (not shown).

Figure 7A:
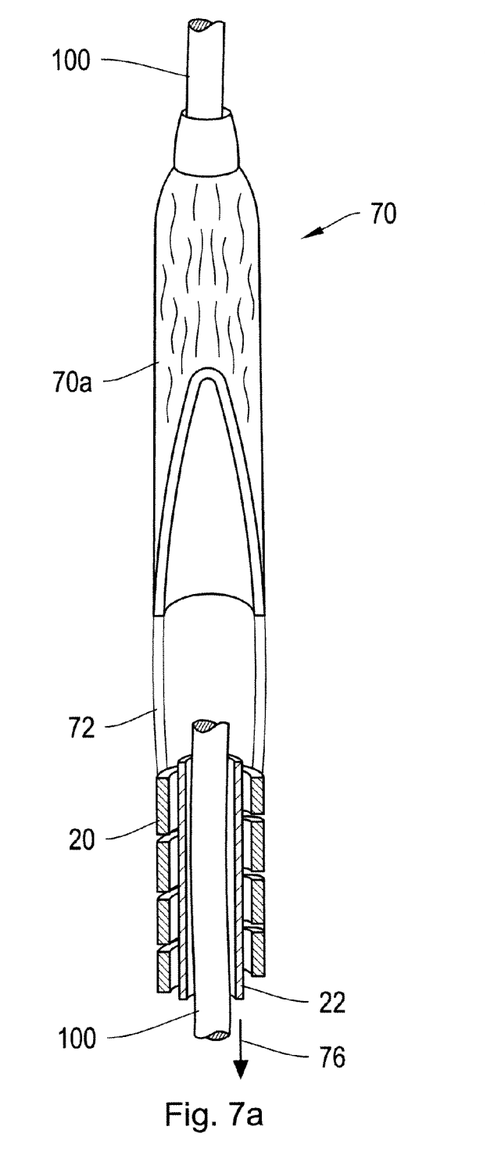
FIGS. 7a and 7b show schematically the guidewire stop of FIG. 2a with an attached embolic protection filter.
Figure 7B:
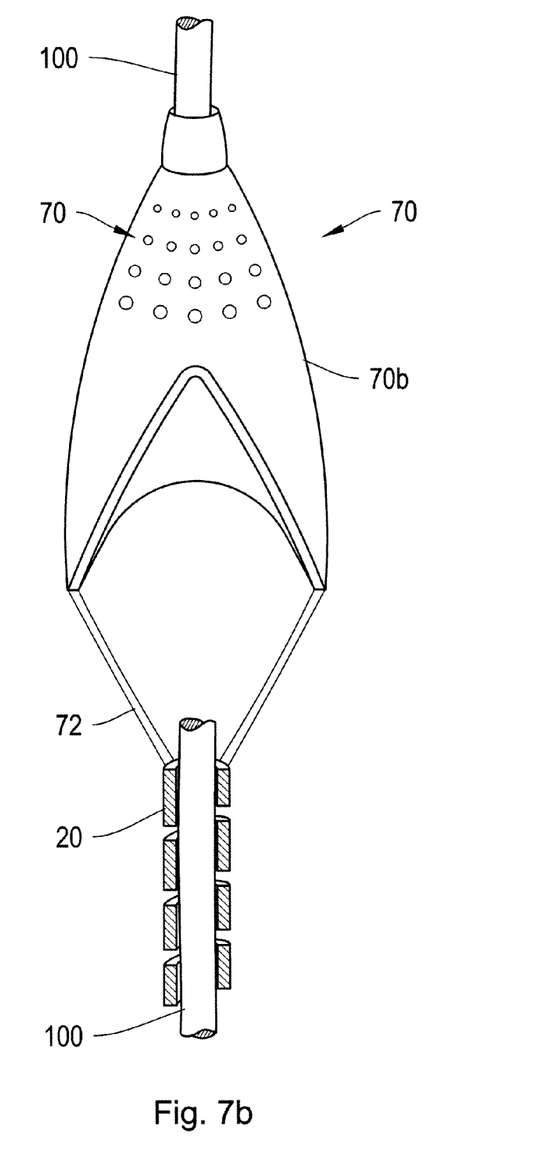

FIGS. 7a and 7b show a schematic diagram of a filter 70 before deployment 70a and the same filter 70 after deployment 70b. The exemplary filter 70 is shown here as being attached to a guidewire stop 20 of the type depicted in FIG. 2a by a plurality of struts forming a filter frame 72. Coil spring 20 can be locked on guidewire 100 by withdrawing restrainer sheet 22 proximally in the direction indicated by arrow 76. Although not shown, guidewire 100 typically extends continuously through the entire length of filter 70, 70b.

It will be understood that the other coil spring locking elements illustrated in the drawings can cooperate with the depicted embolic filter and with various other medical devices used, for example, in intravascular procedures in the manner illustrated in FIGS. 6 and 7a, 7b.

While embodiments of the present invention have been described with reference to an embolic filter, it will be appreciated that the lock of the present invention may be employed with any medical device that is designed to be introduced into a body lumen through the use of a guidewire. Medical devices, such as, but not limited to, urological, neurological, or cardiological devices, may be implanted temporarily or permanently into a body lumen, for example, via a transcatheter procedure. The guidewire stop of the present invention provides a unique solution for the positioning and optionally locking such devices on bare guidewires.

While the invention is receptive to various modifications, and alternative forms, specific examples thereof have been shown in the drawings and are herein described in detail. It should be understood, however, that the invention is not limited to the particular forms or methods disclosed, but to the contrary, the invention is meant to cover all modifications, equivalents, and alternatives falling with the spirit and scope of the appended claims.

The invention claimed is:

1. An actuatable guidewire stop configured to limit movement of an intravascular device relative to a bare guidewire, comprising:
   a coil spring having an inner lumen with a first diameter when the coil spring is restrained in an unlocked configuration relative to the guidewire, the coil spring being configured to slideably and rotationally receive the guidewire in the unlocked configuration, the inner lumen having a second diameter when the coil spring is unrestrained, the coil spring being configured to frictionally engage the guidewire in a locked configuration while unrestrained, the second diameter being smaller than the first diameter, the coil spring including turns having at least one protrusion disposed on a turn of the coil spring and adapted for engagement with a corresponding recess disposed on an adjacent turn of the coil spring, the at least one protrusion interlocking with the corresponding recess to restrain the coil spring in the unlocked configuration, and
   a disengagement member operable to disengage the at least one protrusion from the corresponding recess, the coil spring being adapted to transition into the locked configuration by disengaging the at least one protrusion from the corresponding recess.

2. The guidewire stop of claim 1, wherein the recess has a predetermined undercut angle.

3. The guidewire stop of claim 1, wherein the disengagement member includes an actuator operatively coupled to a proximal portion of the coil spring for changing the coil spring from the unlocked configuration to the locked configuration upon application of a longitudinal pulling force.

4. The guidewire stop of claim 3, wherein the coil spring is retained in a retainer tube which encircles the coil spring and includes an inward pointing shoulder supporting the coil spring on an outer shoulder formed on the coil spring to counteract the longitudinal pulling force.

5. The guidewire stop of claim 4, wherein the retainer tube is part of a delivery catheter.

6. An intravascular filter device, comprising:
   a filter frame disposed about a bare guidewire;
   a filter membrane operatively coupled to the filter frame; and
   a coil spring attached to the filter frame, said coil spring having an inner lumen with a first diameter configured to slideably and rotationally receive the guidewire in an unlocked configuration, and frictionally engage the guidewire in a locked configuration, wherein in the locked configuration the inner lumen has a second diameter smaller than the first diameter,
   wherein the coil spring comprises turns having at least one protrusion disposed on a turn of the coil spring and adapted for engagement with a corresponding recess disposed on an adjacent turn of the coil spring,
   wherein the at least one protrusion interlocks with the corresponding recess to maintain the coil spring in the unlocked configuration, and
   wherein the coil spring transitions into the locked configuration by disengaging the at least one protrusion from the corresponding recess.

7. The device of claim 6, wherein the recess has a predetermined undercut angle.

8. The device of claim 6, further comprising a disengagement member including an actuator operatively coupled to a proximal portion of the coil spring for changing the coil spring from the unlocked configuration to the locked configuration upon application of a longitudinal pulling force.

9. A method for locking a guidewire stop onto a bare guidewire at a desired location along the length of the guidewire, comprising;
   advancing the guidewire stop configured as a coil spring having coil turns with at least one protrusion disposed on a turn of the coil spring and adapted for engagement with a corresponding recess disposed on an adjacent turn of the coil spring, and an inner lumen with a first diameter configured to slideably and rotationally receive the guidewire in an unlocked configuration, wherein the at least one protrusion interlocks with the corresponding recess to maintain the coil spring in the unlocked configuration; and elongating the coil spring by applying a pulling force in a longitudinal direction, thereby disengaging the at least one protrusion from the corresponding recess to transition the coil spring from the unlocked configuration to a locked configuration and causing the coil spring to frictionally engage the guidewire in the locked configuration and lock the guidewire stop on the guidewire, wherein in the locked configuration the inner lumen has a second diameter smaller than the first diameter.

\* \* \* \* \*